United States Patent [19]
Brake et al.

[11] Patent Number: 5,229,528
[45] Date of Patent: Jul. 20, 1993

[54] RAPID DEPOLYMERIZATION OF POLYHYDROXY ACIDS

[75] Inventors: Loren D. Brake, Wilmington; Narayanan S. Subramanian, Hockessin, both of Del.

[73] Assignee: E. I. du Pont de Nemours and Company, Wilmington, Del.

[21] Appl. No.: 796,273

[22] Filed: Nov. 22, 1991

[51] Int. Cl.$^5$ .................. C07D 319/00; C07C 69/68; C07C 59/08
[52] U.S. Cl. .................. 549/274; 560/179; 562/580; 562/589
[58] Field of Search ............. 560/179; 562/580, 589; 549/274

[56] References Cited

U.S. PATENT DOCUMENTS

| | | | |
|---|---|---|---|
| 2,231,953 | 2/1941 | Ruxicka | 92/17 |
| 3,284,417 | 11/1966 | Hostettler et al. | 260/78.3 |
| 3,578,700 | 5/1971 | Klootwijk et al. | 260/484 |
| 4,727,163 | 2/1988 | Bellis | 549/274 |
| 4,797,468 | 1/1989 | De Vries | 528/354 |
| 4,835,293 | 5/1989 | Bhatia | 549/274 |

FOREIGN PATENT DOCUMENTS

90/01521 2/1990 PCT Int'l Appl. .

*Primary Examiner*—José G. Dees
*Assistant Examiner*—Porfirio Nazario

[57] ABSTRACT

Recovery of polyhydroxy acids (PHAs) from waste containing high molecular weight polyhydroxy acid polymer by depolymerizing the PHA in water at elevated temperature and pressure.

10 Claims, No Drawings

RAPID DEPOLYMERIZATION OF POLYHYDROXY ACIDS

BACKGROUND OF THE INVENTION

1. Field of the Invention

The present invention relates to the rapid depolymerization of polyhydroxy acids (PHAs) in water by heating under pressure. More specifically, the present invention relates to the recovery of hydroxy acid value from a polyhydroxy acid polymer-containing source such as food container trash.

2. Description of Related Art

Shaped articles of high molecular weight (at least 10,000, and normally 15,000 to 500,000 MW) polyhydroxy acids (PHA), particularly as polylactic acid (PLA, polylactide), and polyglycolic acid (PGA, polyglycolide), and copolymers thereof, have been known for years. An important property of these polymers is that they are slowly hydrolyzable and thereafter biodegradable to environmentally benign by-products. Consequently high molecular weight PHA polymer shaped articles are finding increasing application as replacements for polystyrene and other non-degradable polymers in products that will degrade in a landfill, such as fast food containers (Sinclair et al., WO90/01521, 22 Feb. 1990).

While this is a significant step in minimizing litter and long-term landfill disposal, discarding high molecular weight polyhydroxy acid articles for natural destruction by hydrolysis has the cost penalty of discarding the valuable polyhydroxy acid.

Although the hydrolysis of PHAs is well known, heretofore it has not been achievable in a time frame to permit recovery from other insoluble ingredients and reuse of the valuable hydroxy acid (HA) moities. In fact, although degradable, the time for degradation of high molecular weight PHAs is so long as not to offer a significant lessening burden on landfills.

Thus, there is a need for an economical method to recover and recycle the polyhydroxy acid content of this source of insoluble waste material and avoid burdening landfills with this waste.

The most economical routes for PHA production start with the acid such as lactic acid. The acid is converted to an ester, dimerized to a cyclic ring such as lactide, which is then polymerized to PHA. This is a complicated and costly process. See Bhatia U.S. Pat. No. 4,835,293 (May 30, 1989); Bellis U.S. Patent No. 4,727,163 (Feb. 23, 1988); Klootwijk U.S. Pat. No. 3,578,700; Hostettler et al. U.S. Pat. No 3,284,417; and De Vries U.S. Pat. No. 4,797,468 (Jan. 10, 1989).

Bhatia, U.S. Pat. No. 5,136,053 discloses the depolymerization of low molecular weight oligomers remaining after PHA polymerization. This patent application does not address the problem of recovery of the monomeric values from used high molecular weight PHA articles.

Copending and commonly assigned, U.S. patent applications Ser. Nos. 071,797,502; 071,797,503; 071,796,272; and 071,796,274 disclose the recovery of PHA's, respectively, in the presence of an alcohol and an acid catalyst; in water and acid; in the presence of specific amines, and in the presence of water and lower alkyl alcohol.

The aforementioned patents and patent applications are incorporated herein by reference.

SUMMARY OF THE INVENTION

The present invention provides a method of depolymerizing a high molecular weight solid polyhydroxy acid polymer to a lower molecular weight moiety comprising mixing said polymer with water at sufficient temperature and pressure for a sufficient time to significantly depolymerize the polymer. In one embodiment of the invention the polymer is selected from group consisting of polylactide, polyglycolide, and polymers containing a major proportion of polylactide or polyglycolide copolymerized with up to 30% of another monomer selected from the group consisting of epsilon-caprolactone, delta-valerolactone, 1,5-dioxepen-2-one, 1,4-dioxan-2-one, beta-butyrolactone, beta-propiolactone, 6-methyl-2,5-morpholinedione and mixtures thereof. Typically the temperature of the process is in the range 100° to 200° C. and the time is in the range of ¼ to 16 hours.

The present invention further provides a process for recoverying polyhydroxy acid and hydroxy acid value from a polyhydroxy acid polymer-containing source comprising the steps of:

(a) contacting a polyhydroxy acid polymer-containing material, wherein said polyhydroxy acid polymer-containing material is contaminated with or constitutes trash, with at least one mole of water per mole of hydroxy acid equivalent of said polyhydroxy acid polymer while maintaining the resulting mixture at sufficient temperature and pressure for a sufficient time to depolymerize said polymer and form a liquid phase of enhanced monomer and oligomer hydroxy acid value; and (b) thereafter isolating and recovering said liquid phase.

DESCRIPTION OF THE INVENTION

The present invention is a process for economically rapid depolymerization of PHAs and recovery of the valuable PHAs without resorting to landfill of the PHA products.

Specifically, the present invention relates to an inexpensive depolymerization of high molecular weight PHAs of at least 10,000 and normally 15,000–500,000 MW often from mixed waste such as insoluble fast food waste. In the process of the present invention PHA in an aqueous medium is subjected to adequate heat and pressure to cause rapid and economical depolymerization of the PHA. When depolymerization is completed to the desired extent, the hydroxy acid (HA) product and PHA oligomers as an aqueous fluid can be recycled to PHA manufacture. Preferably, depolymerization is continued long enough to yield a PHA depolymerization product at a concentration of at least 10%, and preferably greater than 70%.

When adequate pressure is used, depolymerization conversion to the monomer and lower molecular weight oligomers in excess of 60%, and normally in the range of 70–100%, of theoretical is achieved.

This process is used for the depolymerization of the high molecular weight PHAs, and co- and ter-polymers therewith. It is most useful in the depolymerization of polylactide, polyglycolide and copolymers thereof; also it is useful for PHAs containing these polymer moities polymerized with other monomers. These co- and ter-polymers preferably contain at least 70% of PLA and PGA moities, and not more than 30% of the other monomer. Examples of other suitable monomer units are: epsilon-caprolactone, delta-valerolactone,
1,5-dioxepan-2-one,
1,4-dioxan-2-one,
beta-butyrolactone,
beta-propiolactone,
6-methyl-2,5-morpholinedione.

Other monomer units present in the PHA to be depolymerized are not critical, the present process having wide applicability in depolymerizing and recovering the monomer value of PHAs.

The amount of water used affects the time required to carry out the depolymerization and the percent conversion. Normally a molar ratio of water to PHA (on an acid unit basis) in the range of 1:1 to 5:1, preferably 1.5:1 to 2:1, is used. Since an excess of water favors depolymerization, preferably a substantial excess is used, but not so much as to make product recovery an excessive expense.

The important aspect of the present invention is to use pressures, and so temperatures, adequate to cause the rapid depolymerization of the PHAs, but not severe enough to form undesirable degradation products.

Temperatures normally in the range of 75°–250° C. or higher, preferably 100°–200° C., are employed. In many cases overall economics and reaction kinetics dictate running the process at atmospheric pressure, although elevated pressure sometimes is needed to reach the necessary temperatures for depolymerization. However, it may be desirable to use elevated pressures up to about 500 psi or higher, preferably 50–200 psi, when high rates are desired. Normally autogenous pressure is adequate.

A very important economical aspect of the present process is the speed of the depolymerization. By selecting optimal reaction conditions, particularly pressure and temperature, significant quantities of PHA can be batch depolymerized often in 1 hour and even in as little as 15 minutes. Reactor design, i.e., agitation, etc., also plays an important role in reaction rate. Where speed is less a factor than other economies, batch times as long as 16 hours may be appropriate.

Continuous process depolymerization is also possible, such as with the feed materials being continuously introduced into the first depolymerization stage of a multistage system, and the monomer and oligomer product being recovered from the last stage.

The following examples illustrate the preferred practice of the present invention.

EXAMPLE 1

A mixture of 75 grams polylactide (300,000 MW) and 38 grams water is heated at 150° C. for one hour in a pressure vessel under autogenous pressure of 95 psig. The solid product depolymerizes to lactic acid and low molecular weight oligomers to form an 80% fluid of the lactic acid values in water that can be easily pumped and transported for conversion to polymer for reuse.

EXAMPLE 2

A mixture of 75 grams polylactide and 50 grams water is heated at 170° C. for 30 minutes in a pressure vessel under autogenous pressure of 110 psig. The solid product depolymerizes to lactic acid and low molecular weight oligomers in an aqueous fluid that can be pumped and transported for conversion to polymer for reuse.

EXAMPLES 3–6

The process of Example 2 is repeated using the following ingredients with similar results.

| Example | Polymer |
| --- | --- |
| 3 | Copolymer of 80% lactic acid and 20% glycolic acid |
| 4 | Copolymer of 90% lactic acid and 10% glycolic acid |
| 5 | Copolymer of 80% lactic acid and 20% epsilon-caprolactone |
| 6 | Copolymer of 90% lactic acid and 10% beta-propiolactone |

EXAMPLE 7

A mixture of 100 grams polylactide and 100 grams water is heated for 3 hours at 120° C. in a pressure vessel under autogenous pressure. The product is a liquid containing the polylactic acid depolymerization moities.

What is claimed is:

1. The process of depolymerizing a high molecular weight solid polyhydroxy acid polymer to monomeric hydroxy acid monomer and low molecular weight oligomers comprising mixing said polymer with water at sufficient temperature and pressure for a sufficient time to significantly depolymerize the polymer, said temperature and pressure being insufficient to form undesirable degradation products.

2. The process of claim 1 wherein the pressure is autogenous pressure.

3. The process of claim 1 wherein the polymer contains at least a major proportion of polylactide.

4. The process of claim 1 wherein the polymer is polylactide.

5. The process of claim 1 wherein said polymer is selected from group consisting of polylactide, polyglycolide, and polymers containing a major proportion of polylactide and polyglycolide polymerized with up to 30% of another monomer selected from the group consisting of epsilon-caprolactone, delta-valerolactone, 1,5-dioxepen-2-one, 1,4-dioxan-2-one, beta-butyrolactone, beta-propiolactone, 6-methyl-2,5-morpholinedione and mixtures thereof.

6. The process of claim 2 said temperature is in the range of 100°–200° C. and high enough to depolymerize said polymer.

7. The process of claim 2 wherein the time is in the range of ¼–16 hours and sufficient to reach molar equilibrium depolymerization.

8. The process of claim 1 wherein the produce of depolymerization is the primarily monomeric hydroxy acid.

9. The process of claim 1 wherein the water to polyhydroxy acid molar ratio is in the range of 1:1 to 5:1.

10. A process for recovering polyhydroxy acid and hydroxy acid value from a polyhydroxy acid polymer-containing source comprising the steps of:
(a) contacting a polyhydroxy acid polymer-containing material, wherein said polyhydroxy acid polymer-containing material is contaminated with or constitutes trash, with at least one mole of water per mole of hydroxy acid equivalent of said polyhydroxy acid polymer while maintaining the resulting mixture at sufficient temperature and pressure for a sufficient time to depolymerize said polymer and form a liquid phase of enhanced monomer and oligomer hydroxy acid value, said temperature and pressure being insufficient to form undesirable degration products; and,
(b) thereafter isolating and recovering said liquid phase.

* * * * *